United States Patent [19]

Richards et al.

[11] 4,139,915
[45] Feb. 20, 1979

[54] ARTIFICIAL INTRAOCULAR LENS

[75] Inventors: William Richards, Medway; Bernard Grolman, Worcester, both of Mass.

[73] Assignee: American Optical Corporation, Southbridge, Mass.

[21] Appl. No.: 779,384

[22] Filed: Mar. 21, 1977

[51] Int. Cl.² .......................... A61F 1/16; A61F 1/24
[52] U.S. Cl. .......................................... 3/13; 16/108; 29/517; 140/76
[58] Field of Search ................. 3/13; 140/76; 16/108, 16/109; 29/516, 517; 128/335.5, 339

[56] References Cited
U.S. PATENT DOCUMENTS

| 2,188,841 | 1/1940 | McDonald | 16/109 X |
| 3,311,110 | 3/1967 | Singerman et al. | 128/335.5 |
| 3,673,616 | 7/1972 | Fedorov et al. | 3/13 |
| 3,866,249 | 2/1975 | Flom | 3/13 |
| 3,991,426 | 11/1976 | Flom et al. | 3/13 |
| 3,996,626 | 12/1976 | Richards et al. | 3/13 |

Primary Examiner—Ronald L. Frinks
Attorney, Agent, or Firm—Jeremiah J. Duggan; H. R. Berkenstock, Jr.

[57] ABSTRACT

A lens suitable for implantation in the eye is provided with iris clips formed of plastic filaments each having at least one of its ends fastened to the lens. Ends of the clips to be fastened are ferruled for secure and permanent affixation.

8 Claims, 7 Drawing Figures

ARTIFICIAL INTRAOCULAR LENS

BACKGROUND OF THE INVENTION

1. Field of the Invention

This invention relates to improvements in ophthalmology and more particularly to improvements in artificial intraocular lenses (pseudophakoi) used for the correction of aphakia and re-establishment of binocularity in aphakia.

2. Discussion of the Prior Art

Well-fixed and well-centered intraocular lens implants are known to produce stable retinal images with stable space localization and offer the best chance of re-establishment of binocularity in cases of aphakia.

Many techniques of lens implantation, including suturing to the ciliary muscle as disclosed in U.S. Pat. No. 3,711,870 and iris diaphragm fixation as disclosed in U.S. Pat. No. 3,673,616 have been used. The latter is considered to be a safe procedure giving good stability and the present invention deals with improvements in this general type of pseudophakos. More particularly, the invention relates to improvements in "iridocapsular" and/or "iris clip" implants which have haptic sections respectively comprised of posterior and both posterior and anterior fastening elements all of which will be referred to hereinafter as iris clips. The iris clips may be in the form of loops and/or struts fastened to and extending away from the lenses.

Heretofore, iris clips have been formed of biologically inert metal wires which are at least in some respects, less than optimum in purpose. In this connection, even when formed of the least dense of useful metals or alloys, such loops and/or struts are relatively heavy in the eye, opaque and unaesthetic, less than optimally manipulatable before and/or during surgical implantation procedures and expensive both from the standpoint of precious metal cost and the intricacy of loop manufacture, not to mention the wire forming operation itself.

An already recognized alternative to the use of metals for iris clips is that of using plastics, i.e. transparent or translucent filament or fiber formed of nylon, polymethylmethacrylate or other similarly chemically pure and biologically inert materials known and available in the art. Fastening of these usually difficult to handle thin sections of plastics, however, has heretofore presented serious manufacturing problems. Staking, press fitting or interference fitting and other such attempts to fasten plastic iris clips in place are inherently difficult and tedious operations attended by high scrap yield and usually less than complete assurance against loosening or disconnection of parts during or following surgical implantation.

The use of adhesives which may avoid some of the problems of mechanical fixation procedures is, on the other hand, often frowned upon for reasons of possibility, however small, of dangerous loosening and/or disasterous detachment of parts in the eye as a result of attack upon the bond or adhesive itself by ocular fluids.

In view of the foregoing, it is a principle object of this invention to overcome present difficulties and drawbacks attending the fixing of iris clips to lenses of pseudophakoi and more particularly to overcome the problems and difficulties currently experienced in providing these lenses with iris clips formed of plastic materials.

More specifically, it is an object of the invention to provide novel and improved means and method for fixing plastic iris clips to lenses of pseudophakoi wherewith the attachment can be made simply efficiently and economically and especially with an assurance of permanence throughout the expected useful life of the product.

Other objects and advantages of the invention will become apparent from the following description.

SUMMARY OF THE INVENTION

The foregoing objects and their correlaries are accomplished by ferruling ends of plastic iris clips to be attached to lenses of pseudophakoi. It is contemplated that the ferruling be staked, crimped, wedged or fused to the plastic filament or fiber used to form the iris clips and, in turn, anchored in the lens with cold flow of lens material therearound and/or fused to the lens material.

The iris clips may comprise struts each having one end only ferruled and fixed to the lens of a pseudophakos and/or loops each having their opposite ends ferruled and anchored.

Greater details of the invention will become more readily apparent from the following description when taken in conjunction with the accompanying drawings.

IN THE DRAWINGS

DESCRIPTION OF THE PREFERRED EMBODIMENTS

Figure 1:
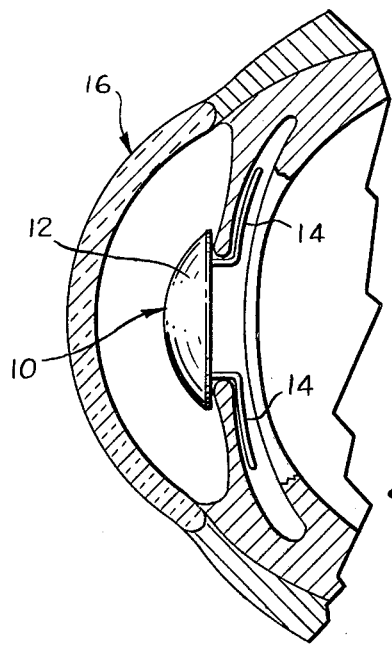
FIG. 1 is an illustration, in cross-section of an eye in which there is diagrammatically illustrated an implanted pseudophakos of a type embodying the invention.
Figure 2:
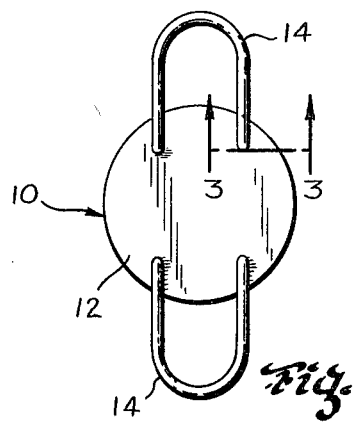
FIG. 2 is a rear elevational view of the pseudophakos.

Referring more particularly to FIGS. 1 and 2 of the drawings, pseudophakos 10 comprises a lens 12 having a pair of posterior iris clips 14 for fixturing within eye 16. This particular form of pseudophakos is commonly referred to as an "iridocapsular lens" or "two-loop lens." Its fixation is in the iridocapsular cleft substantially as illustrated in FIG. 1.

Lens 12 is formed of a material which is biologically inert, i.e. not susceptible to absorption or deterioration by body fluids and capable of being well tolerated by the human body when implanted. Exemplary materials are methylmethacrylate resins such as those available under the tradenames "Lucite" and "Plexiglas" and biologically neutral chemically pure polymethylmethacrylates or biologically inert polymeric materials.

According to the present invention, iris clips 14 are also formed of a chemically pure biologically inert plastic materials. Nylon and polymethylmethacrylate are exemplary. Opposite ends of the loops are ferruled, e.g. as illustrated in FIGS. 3-6, for purposes of rendering their attachment to lens 12 secure and permanent.

Figure 3:
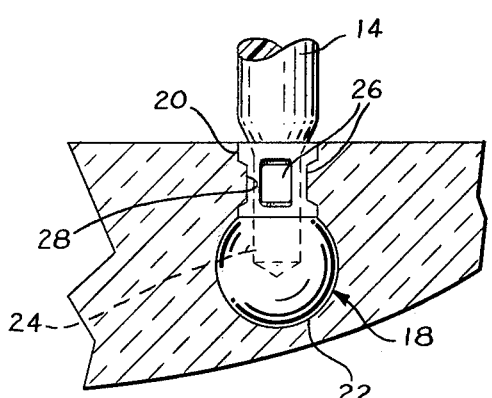
FIG. 3 is a greatly enlarged cross-sectional view taken at approximately the position of line 3—3 of FIG. 2 and illustrating one of the preferred embodiments of the invention.

Referring more particularly to FIG. 3 wherein one end of an iris clip 14 is illustrated, ferrule 18 having shank 20 is terminated with ball portion 22. Iris clip 14 is fitted into opening 24 in ferrule 18 which extends through shank 20 at least partially into ball portion 22 as illustrated with broken lines. With iris clip 14 so in place, shank 20 is mechanically laterally swaged, e.g. at points 26 thereabout, so as to permanently fix ferrule 18 upon iris clip 14 preventing withdrawal of clip 14.

It should be understood that while ferrule 18 is illustrated as being embedded in lens 12 in FIG. 3, its attachment to iris clip 14 is effected prior to being embedded in lens 12.

The fastening of a ferruled end of iris clip 14 to lens 12 is accomplished by forcing ferrule 18 into a hole 28 provided in lens 12 and which is of a smaller diameter than that of ball portion 22 thereby causing cold flow of material of lens 12 to neck closely and tightly about shank 20 as illustrated in FIG. 3. This cold flow anchoring scheme per se is illustrated in U.S. Pat. No. 3,996,626. This patent, however, deals with matters of anchoring iris clips of wire (all metal). Nevertheless, those interested in details of method, tools used and/or a preferred technique for anchoring enlarged ends of iris clips may refer to this issued patent. In the present invention, however, it is rigid ferrule 18 which is forced into lens 12 carrying along with it the plastic iris clip 14. Hole 28 in lens 12 has been depicted as already having been deformed by cold flow of the material of lens 12 about shank 20 of ferrule 18. Use of the expression "cold flow" herein is not intended to exclude the use of heat to enhance lens material flow provided there is no actual melting of the material.

Figure 4:
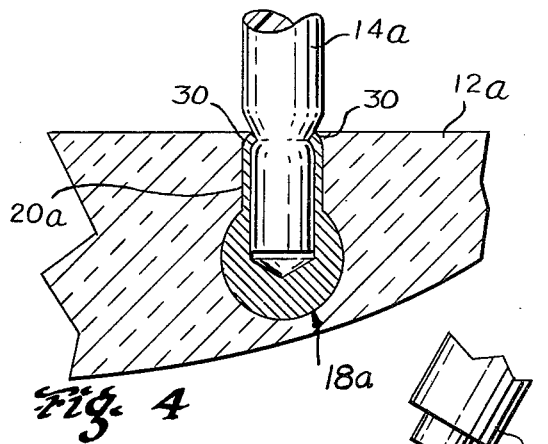
FIGS. 4, 5 and 6 are similarly enlarged cross-sectional views of other embodiments of the invention.

In the FIG. 4 embodiment of the invention ferrule $18_a$ is fastened to iris clip $14_a$ by necking or turning spurs 30 from the rim of shank $20_a$ into iris clip $14_a$ e.g. with a cutting and forming tool and/or with other such means designed to perform the operation. Tool selection and/or designing for accomplishing the ferruling of either the FIG. 3 or FIG. 4 embodiment of the invention would be well within the realm of ordinary skill in the art and, accordingly, will not be dealt with herein. For example, this ferruling could, notwithstanding difficulties, be accomplished with hand pliers or the like in the absence of more sophisticated tooling.

After fixing to iris clip $14_a$, ferrule $18_a$ may be anchored in lens $12_a$ in the manner already described in connection with the FIG. 3 embodiment of the invention.

Figure 5:
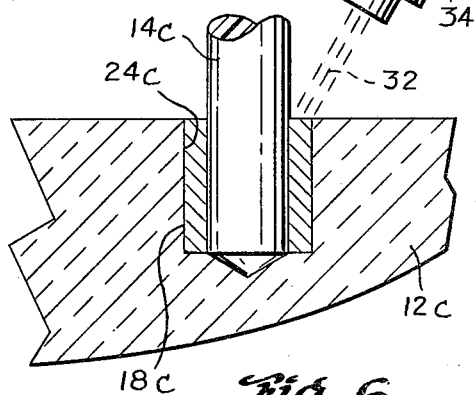

The embodiment of the invention illustrated in FIG. 5 comprises ferrule $18_b$ having shank $20_b$, ball portion $22_b$ and opening $24_b$ therewithin, all of which are contemplated as being similar to corresponding parts of ferrules 18 and $18_a$ prior to swaging and/or other deformation of shanks 20 and $20_a$. In the FIG. 5 embodiment of the invention, ferrule $18_b$ is preferably but not necessarily forcefully fitted onto an end of iris clip $14_b$ and fused thereinplace, e.g. by application of laser energy. A neodymium laser may be used for this purpose. The selection of type of laser and output energy level needed may be easily determined by the artisan and requires means of producing heat for fusing plastic to metal may be used.

In any case, it is contemplated that the ferruling of iris clip $14_b$ be completed prior to anchoring of the iris clip in lens $12_b$. Hereagain, anchoring may be accomplished in the manner described relative to the embodiments of FIGS. 3 and 4. It should also be understood that the operation of fusing iris clips to ferruling may also be used in the structures illustrated in FIGS. 3 and 4 if added strength and/or security of bond is desired.

Figure 6:
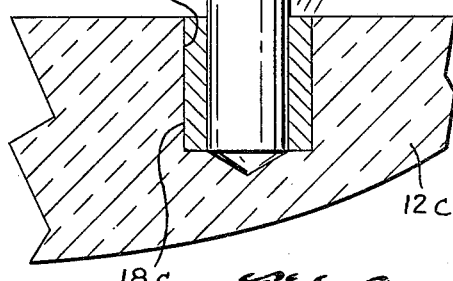

The FIG. 6 embodiment of the invention involves a hollow cylindrical, i.e. tubular, ferrule $18_c$ which is preferably tightly fitted into an opening $24_c$ in lens $12_c$ and into which iris clip $14_c$ is inserted as illustrated. Having so assembled lens $12_c$, ferrule $18_c$ and iris clip $14_c$ they are all fused together by laser beam 32. Laser 34 and lens $12_c$ may be continuously or periodically moved one relative to another to spot or zonally fuse these components and/or continuously effect fusion circumferentially about iris clip $14_c$. It is contemplated that by similarly applying laser energy to any one or all of ferrules 18, $18_a$, $18_b$ their secureness in lenses 12, $12_a$ and $12_b$ may be enhanced. On the other hand, it should be understood that ferrule $18_c$ may itself be wedged, crimped or otherwise further fixedly secured to iris clip $14_c$.

Figure 7:
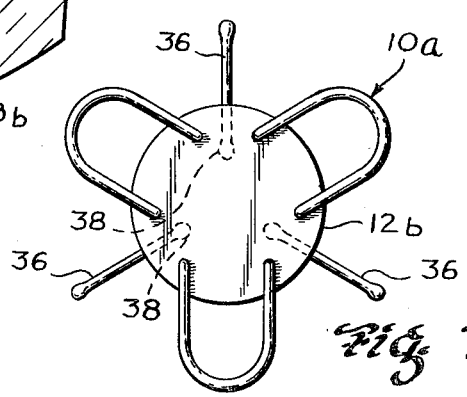
FIG. 7 is a rear elevational view of an alternative form of pseudophakos to which the present invention is applicable.

Referring more particularly to FIG. 7, pseudophakos $10_a$ has been shown only to illustrate another of the great many forms of lens fixturing systems to which the present invention is applicable. It is a practice in some cases, especially after extracapsular extraction, to provide anterior iris clips. These may be of looped configuration or in the form of struts. Struts 36 in FIG. 7 are exemplary and any one or a variation of the ferrulings of FIGS. 3-6 may be used to anchor end 38 of each strut in lens $12_d$.

As in the case of prior art use of all metal iris clips, ferrules of the present invention are required to be formed of biologically inert metals such as platinum or titanium, the latter being preferred for its durability and lightness of weight. A hard plastic may also be used.

As an illustration of the intricacies of the present highly specialized form of ophthalmic optics, a typical lens 12 diameter would be from 4 to 5 mm with ferrules 18, $18_a$, $18_b$ or $18_d$ having maximum outer diameters of approximately 0.137 mm. It is also contemplated that shanks 20, 28, and $20_b$ be of approximately 0.129 mm with iris clips 14, $14_a$, $14_b$ and $14_c$ or struts 36 having an approximately similar 0.129 mm outer diametral dimension.

Those skilled in the art will readily appreciate that there are various other modifications and adaptations of the precise form of the invention here shown and that the foregoing illustrations are not to be interpreted as restrictive beyond that necessitated by the following claims.

We claim:

1. A pseudophakos comprising:
   a lens formed of materials suitable for implantation in the eye and having at least one opening extending thereinto;
   an iris clip formed of a filament of plastic materials; and
   a rigid ferrule affixed to at least one end of said clip, said ferrule being entered into said opening and secured against withdrawal therefrom.

2. A pseudophakos according to claim 1 wherein said ferrule is swaged against said filament.

3. A pseudophakos according to claim 1 wherein said ferrule is crimped against said filament.

4. A pseudophakos according to claim 1 wherein said ferrule is fused to said filament.

5. A pseudophakos according to claim 1 wherein said ferrule is provided with a shank and an enlarged ball portion, an opening extending into said shank for receiving said end of said filament, said ball portion being of a diametral size greater than that initially afforded said opening in said lens and said ferrule being fixed against withdrawal by material of said lens having been displaced by said ball portion into tightly necked relationship about said shank.

6. A pseudophakos according to claim 1 wherein said ferrule is of tubular configuration and placed in said opening in said lens with said one end of said clip extended into said tubular ferrule; said end of said clip, ferrule, and adjacent material of said lens all being fused together.

7. A pseudophakos according to claim 2 wherein said swaged ferrule is additionally fused to said filament.

8. A pseudophakos according to claim 3 wherein said crimped ferrule is additionally fused to said filament.

* * * * *